United States Patent [19]

Giani et al.

[11] Patent Number: 4,594,190

[45] Date of Patent: Jun. 10, 1986

[54] QUATERNARY SALTS OF DIBENZO[1,4]DIAZEPINONES, PYRIDO-[1,4]BENZODIAZEPINONES, PYRIDO[1,5]BENZODIAZEPINONES WITH ANTIULCER, ANTISECRETORY, SPASMOLYTIC AND ANTIMUSARINIC ACTIVITIES

[75] Inventors: Roberto Giani; Ettore Parini; Giancarlo Tonon, all of Milan, Italy

[73] Assignee: Dompe' Farmaceutici S.p.A., Milan, Italy

[21] Appl. No.: 609,102

[22] Filed: May 9, 1984

[30] Foreign Application Priority Data

May 17, 1983 [IT] Italy ................. 21135 A/83

[51] Int. Cl.$^4$ ................. C07D 401/04; C07D 401/06; A61K 31/33
[52] U.S. Cl. ................. 260/239.3 R; 260/239 BD; 260/239 DD; 260/239.3 T; 260/243.3; 260/244.4; 260/245.7; 514/220
[58] Field of Search ..... 260/243.3, 239 BD, 239 DD, 260/244.4, 245.7, 239.3 R, 239.3 T; 514/220

[56] References Cited

U.S. PATENT DOCUMENTS 4,556,653 12/1985 Giani et al. ................. 514/220

FOREIGN PATENT DOCUMENTS 1795183 7/1972 Denmark .
2724478 12/1978 Denmark .
1505795 12/1967 France .

OTHER PUBLICATIONS

Monro et al, J. Med. Chem., 6, 255, 1963.
Thomae, Chem. Abst., 90-137875s (1979).
Schmidt et al, Chem. Abst., 73-77292m (1970).
Burger, Medicinal Chem., 2nd Edition, 1960, pp. 480-481.

Primary Examiner—Donald G. Daus
Assistant Examiner—Cecilia Shen
Attorney, Agent, or Firm—Walter H. Schneider

[57] ABSTRACT

Quaternary salts of 11-acyl derivatives of 5,11-dihydro-6H-pyrido[2,3-b][1,4]benzodiazepin-6-one, 6,11-dihydro-5H-pyrido[2,3-b][1,5]benzodiazepin-5-one and 5,10-dihydro-11H-dibenzo[b,e][1,4]diazepin-11-one are described.

Said quaternary salts are endowed with antiulcer, antisecretory, spasmolytic and antimuscarinic activity.

9 Claims, No Drawings

QUATERNARY SALTS OF DIBENZO[1,4]DIAZEPINONES, PYRIDO-[1,4]BENZODIAZEPINONES, PYRIDO[1,5]BENZODIAZEPINONES WITH ANTIULCER, ANTISECRETORY, SPASMOLYTIC AND ANTIMUSARINIC ACTIVITIES

The present invention refers to compounds having general formula I

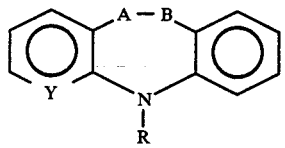

wherein
Y is N or CH,
A is NH,
B is C=O or C=S or vice versa,
R is a group of formula

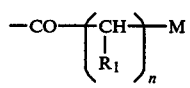

wherein $R_1$ is hydrogen or $C_1$-$C_4$ alkyl and n is 1 or 2, M represents one of the following groups

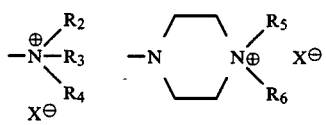

wherein $X^-$ is the anion of an halogenidric acid $R_2$, $R_3$ and $R_4$, which may be the same or different, represent linear or branched $C_1$-$C_4$ alkyl, cycloalkyl, pivaloyloxymethyl, benzyl or $R_2$ has one of said meanings and $R_3$ and $R_4$ together form one of the following cyclic residues

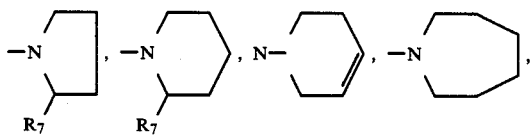

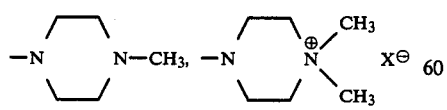

wherein
$R_7$ is hydrogen or methyl and $X^\ominus$ has the above defined meaning, or
$R_2$, $R_3$ and $R_4$, taken together, form one of the following groups:

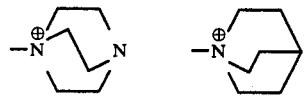

$R_5$ and $R_6$, which can be the same or different, represent methyl, ethyl, benzyl, 3,4-methylenedioxybenzyl or pivaloyloxymethyl.

The compounds of formula I are endowed with interesting pharmaco-therapeutic properties, particularly antisecretory, antiulcer, spasmolytic and antimuscarinic activity.

The invention refers therefore also to pharmaceutical compositions containing as the active principle one or more compounds of formula I or their pharmaceutically acceptable salts. The invention concerns moreover a process for the preparation of the compounds of formula (I).

Compounds I can be prepared starting from the derivatives of formula II

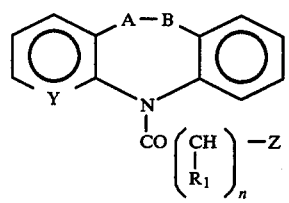

wherein Y, A, B, $R_1$ and n have the above cited meanings and Z is a group of formula

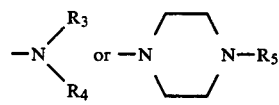

wherein $R_3$, $R_4$ and $R_5$ have the above defined meanings, by reaction with methyl, ethyl, benzyl, cyclohexyl, pivaloyloxymethyl, or 3,4-methylenedioxybenzyl halides.

The reaction is carried out in solvents such as acetonitrile, dioxane, alcohols, benzene, toluene etc. at temperatures ranging from the room temperature to the reflux temperature. The reaction times are ranging from 0.5 to 24 hours.

The compounds II are in turn obtained according to what is described in the Italian Patent Application No. 21134 A/83 in the Applicant's name, i.e. reacting haloacyl derivatives of formula IV,

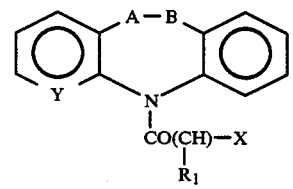

disclosed in the German Pat. Nos. 1,795,183 and 2,724,478, in the French Pat. No. 1,505,795 and in J. Med. Chem. 6, 255, 1963, with amines of formula

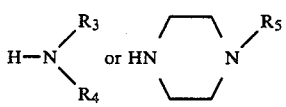

in solvents such as benzene, alcohols or dioxane, optionally in the presence of bases and at temperatures ranging from the room temperature to the solvent reflux temperature.

The compounds I can also be directly obtained from derivatives of formula IV by reaction with tertiary amines of formula

in solvents such as acetonitrile, dioxane, alcohols, at the solvent reflux temperature and with reaction times ranging from 0.5 to 24 hours. Such a synthesis method allows the preparation of the derivatives wherein $R_2$, $R_3$ and $R_4$, taken together, form one of the following groups:

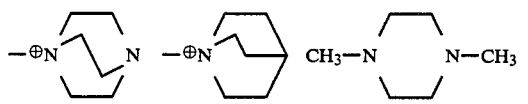

The following examples illustrate further the invention, without limiting in any way the scope thereof.

EXAMPLE 1

11-[2-(4-Methylpiperazin-1-yl)-acetyl]-5,11-dihydro-6H-pyrido[2,3-b][1,4]benzodiazepin-6-one $N^1$-chloromethylate A solution of 11-(2-chloroacetyl)-5,11-dihydro-6H-pyrido[2,3-b][1,4]benzodiazepin-6-one (5 g) and N,N'-dimethylpiperazine (4 g) in acetonitrile (100 ml) was heated to reflux for 2 hours. The mixture was evaporated and the residue, crystallized from methanol, yielded 3 g (42.9%) of 11-[2-(4-methylpiperazin-1-yl)-acetyl]-5,11-dihydro-6H-pyrido[2,3-b][1,4]benzodiazepin-6-one $N^1$-chloromethylate melting at 198°–200° C.

| | Microanalysis | |
| --- | --- | --- |
| | Calc. % | Found % |
| C | 59.77 | 59.84 |
| H | 6.02 | 5.98 |
| N | 17.43 | 17.39 |

EXAMPLE 2

11-[2-(4-Methylpiperazin-1-yl)acetyl]-5,11-dihydro-6H-pyrido[2,3-b][1,4]benzodiazepin-6-one $N^{1,4}$bisiodomethylate A solution of the compound of Example 1 (1 g) and methyl iodide (0.5 ml) in acetonitrile (50 ml) was heated to reflux for 4 hours. After cooling, the precipitated solid was filtered. 0.45 g (33%) of 11-[2-(4-methylpiperazin-1-yl)acetyl]-5,11-dihydro-6H-pyrido[2,3-b][1,4]benzodiazepin-6-one $N^{1,4}$ bisiodomethylate was obtained, melting at 221°–224° C.

| | Microanalysis | |
| --- | --- | --- |
| | Calc. % | Found % |
| C | 39.70 | 39.81 |
| H | 4.28 | 4.33 |
| N | 11.02 | 11.10 |

EXAMPLE 3

11-(2-Dimethylaminoacetyl)-5,11-dihydro-6H-pyrido[2,3-b][1,4]-benzodiazepin-6-one iodomethylate A solution of 11-(2-dimethylaminoacetyl)-5,11-dihydro-6H-pyrido[2,3-b][1,4]benzodiazepin-6-one (3 g) and methyl iodide (1.56 g) in absolute ethanol (50 ml) was stirred at room temperature for 14 hours. The mixture was concentrated to half volume and then left standing to crystallize. After filtration, 2.2 g (50%) of 11-(2-dimethylaminoacetyl)-5,11-dihydro-6H-pyrido[2,3-b][1,4]benzodiazepin-6-one iodomethylate, melting at 249°–250° C., were obtained.

| | Microanalysis | |
| --- | --- | --- |
| | Calc. % | Found % |
| C | 46.59 | 46.54 |
| H | 4.37 | 4.31 |
| N | 12.78 | 12.81 |

EXAMPLE 4

11-[2-(Piperidin-1-yl)acetyl]-5,11-dihydro-6H-pyrido[2,3-b][1,4]benzodiazepin-6-one iodomethylate A solution of 11-[2-(piperidin-1-yl)acetyl]-5,11-dihydro-6H-pyrido[2,3-b][1,4]benzodiazepin-6-one (3 g) and methyl iodide (1.7 g) in acetonitrile (60 ml) was heated to reflux for 2 hours. After cooling, 2.5 g (60%) of 11-[2-(piperidin-1-yl)acetyl]-5,11-dihydro-6H-pyrido[2,3-b][1,4]benzodiazepin-6-one iodomethylate, melting at 243°–245° C., separated.

| | Microanalysis | |
| --- | --- | --- |
| | Calc. % | Found % |
| C | 50.22 | 50.16 |
| H | 4.85 | 4.91 |
| N | 11.71 | 11.75 |

EXAMPLE 5

11-(2-Quinuclidinioacetyl)-5,11-dihydro-6H-pyrido[2,3-b][1,4]benzodiazepin-6-one chloride A solution of 11-(2-chloroacetyl)-5,11-dihydro-6H-pyrido[2,3-b][1,4]benzodiazepin-6-one (5 g) and quinuclidine (3.85 g) in acetonitrile (100 ml) was heated to reflux for 30 minutes. The mixture was then evaporated and the residue triturated with ether.

The crude solid crystallized from isopropanole, yielded 2 g (29%) of 11-(2-quinuclidinioacetyl)-5,11-dihydro-6H-pyrido[2,3-b][1,4]benzodiazepin-6-one chloride, melting at 241°–243° C.

| | Microanalysis | |
| --- | --- | --- |
| | Calc. % | Found % |
| C | 63.23 | 63.18 |
| H | 5.81 | 5.80 |

-continued

| | Microanalysis | |
|---|---|---|
| | Calc. % | Found % |
| N | 14.05 | 14.11 |

EXAMPLES 6-29

Similarly to the methods described in the Examples 1-6, starting from the suitable intermediates, the compounds 6-29 were obtained, whose formulae and chemico-physical characteristics are reported in the following tables.

The compounds of the Examples 12 and 15 have been obtained respectively by reaction of triethylendiamine and N,N'-dimethylpiperazine and the corresponding chloracyl derivatives of formula IV.

TABLE I

| Example n. | R | Yield % | M.p. °C. | Calc. % C | Calc. % H | Calc. % N | Found % C | Found % H | Found % N |
|---|---|---|---|---|---|---|---|---|---|
| 6 | -CH₂-N⁺(CH₃)(2-methylpiperidine) I⁻ | 25 | 226-227 | 51.23 | 5.12 | 11.38 | 51.12 | 5.04 | 11.43 |
| 7 | -CH₂-N⁺(CH₃)(tetrahydropyridine) I⁻ | 34 | 245-247 | 50.43 | 4.44 | 11.76 | 50.45 | 4.38 | 11.70 |
| 8 | -CH₂-N⁺(CH₃)(hexamethyleneimine) I⁻ | 39 | 235-238 | 51.23 | 5.12 | 11.38 | 51.13 | 5.00 | 11.42 |
| 9 | -CH₂N(piperazine-N⁺(CH₃)(CH₂-3,4-methylenedioxyphenyl)) I⁻ | 23 | 236-238 | 52.86 | 4.60 | 11.42 | 52.80 | 4.48 | 11.37 |
| 10 | -CH₂N(piperazine-N⁺(CH₃)(CH₂-phenyl)) I⁻ | 31 | 245-247 | 54.84 | 4.95 | 12.30 | 54.76 | 5.01 | 12.41 |
| 11 | -CH₂⁺N(CH₃)(CH₃)(cyclopropyl) I⁻ | 24 | 226-228 | 52.18 | 5.37 | 11.06 | 52.01 | 5.44 | 11.06 |
| 12 | -CH₂-⁺N(DABCO)N Cl⁻ | 27.5 | 250-252 | 60.07 | 5.55 | 17.51 | 60.12 | 5.48 | 17.55 |
| 13 | -CH₂-CH₂-⁺N(CH₃)(hexamethyleneimine) I⁻ | 67 | 155-157 | 52.18 | 5.37 | 11.06 | 52.09 | 5.41 | 11.11 |

TABLE I-continued

[Structure: dibenzo-diazepinone core with pyridine, NH-C(=O), and N-COR substituent]

| Example n. | R | Yield % | M.p. °C. | Calc. % C | Calc. % H | Calc. % N | Found % C | Found % H | Found % N |
|---|---|---|---|---|---|---|---|---|---|
| 14 | −CH₂−CH₂−N⁺(CH₃)(pyrrolidine) I⁻ | 70 | 138–140 | 50.22 | 4.85 | 11.71 | 50.20 | 4.87 | 11.65 |
| 15 | 4-piperidinyl-N⁺(CH₃)(CH₂OCOC(CH₃)₃) Cl⁻ | 46 | 160–177 (dec.) | 61.66 | 6.41 | 11.50 | 61.38 | 6.37 | 11.64 |
| 16 | −CH₂−N⁺(CH₃)(3,3-dimethylpiperidine) I⁻ | 21 | 216–218 | 52.18 | 5.37 | 11.06 | 51.99 | 5.40 | 11.11 |
| 17 | 4-piperidinyl-N⁺(CH₃)₂ I⁻ | 70 | 208–210 | 50.22 | 4.85 | 11.71 | 50.15 | 4.78 | 11.64 |
| 18 | −CH₂CH₂N(piperazine)-N⁺(CH₃)(CH₂OCOC(CH₃)₃) Cl⁻ | 58 | 189–191 | 60.51 | 6.64 | 13.57 | 60.64 | 6.60 | 13.62 |
| 19 | −CH₂CH₂−N⁺(CH₃)(piperidine) I⁻ | 78 | 153–155 (dec.) | 51.23 | 5.12 | 11.38 | 51.41 | 5.28 | 11.21 |
| 20 | −CH₂−N⁺(CH₃)(2-methylpyrrolidine) I⁻ | 84 | 223–227 (dec.) | 50.22 | 4.85 | 11.71 | 50.41 | 4.94 | 11.70 |
| 21 | −CH₂CH₂−N⁺(CH₃)(2-methylpyrrolidine) I⁻ | 78 | 158–160 | 51.23 | 5.12 | 11.38 | 51.20 | 5.04 | 11.44 |

TABLE II
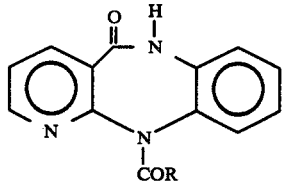
| Example n. | R | Yield % | M.p. °C. | Calc. % C | Calc. % H | Calc. % N | Found % C | Found % H | Found % N |
|---|---|---|---|---|---|---|---|---|---|
| 22 | -CH₂-⊕N(CH₃)(piperazine)-N-CH₃  Cl⊖ | 72 | 208–210 | 59.77 | 6.02 | 17.43 | 56.69 | 6.08 | 17.36 |
| 23 | -CH₂-⊕N(CH₃)(azepane)  I⊖ | 54 | 222–226 | 51.23 | 5.12 | 11.38 | 51.94 | 5.33 | 11.20 |
| 24 | -CH₂-⊕N(CH₃)(3-methylpiperidine)  I⊖ | 57 | 228–230 | 51.23 | 5.12 | 11.38 | 51.08 | 5.08 | 11.19 |
| 25 | -CH₂-⊕N(CH₃)(2-methylpyrrolidine)  I⊖ | 52 | 250–251 | 50.22 | 4.85 | 11.71 | 50.17 | 4.83 | 11.65 |
| 26 | -CH₂⊕N(DABCO)  Cl⊖ | 46 | 215–220 | 60.07 | 5.54 | 17.51 | 59.95 | 5.60 | 17.66 |
| 27 | -CH(CH₃)-⊕N(piperidine)  I⊖ | 71 | 165–170 | 51.23 | 5.12 | 11.38 | 51.36 | 5.22 | 11.41 |
TABLE III
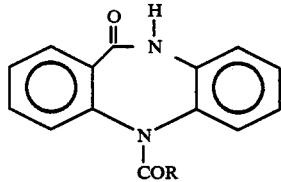
| Example n. | R | Yield % | M.p. °C. | Calc. % C | Calc. % H | Calc. % N | Found % C | Found % H | Found % N |
|---|---|---|---|---|---|---|---|---|---|
| 28 | -CH₂⊕N(CH₃)(2-methylpyrrolidine)  I⊖ | 63 | 140 | 52.84 | 5.07 | 8.80 | 52.80 | 5.12 | 8.74 |

TABLE III-continued

Structure: dibenzodiazepine with C(=O)-NH bridge at top and N-COR at bottom

| Example n. | R | Yield % | M.p. °C. | Microanalysis Calc. % C | H | N | Found % C | H | N |
|---|---|---|---|---|---|---|---|---|---|
| 29 | $-CH_2CH_2\overset{\oplus}{N}(CH_3)\underset{}{}$ (pyrrolidinium) $I^{\ominus}$ | 53 | 222–224 | 53.78 | 5.33 | 8.55 | 53.69 | 5.31 | 8.60 |

The antisecretory and anticholinergic activity in the rat, the acute toxicity in the mouse and the antimuscarinic activity, in comparison with pirenzepine as reference drug, have been determined on the compounds of the invention.

GASTRIC ACID SECRETION IN THE PYLORUS LIGATED RAT

The method of Shay H., Kamarov S. A., Fels, S. S., Meranee D., Gruenstein M., Siplet H., Gastroenterology, 5, 43 (1945) has been used, slightly modified according to the following:

Male Sprague-Dawley rats weighing 150±5 g fasting since 48 hours were used. Pylorus ligation was performed for 4 hours. The products under examination were administered by the oral route immediately after the ligation.

CARBACHOLE SALIVATION IN THE RAT

The method cited by R. Turner: "Parasympatholytic Agents" in R. Turner "Screening Methods in Pharmacology" pag. 137. Academic Press. New York & London 1965, with slight changes, were used. Male Sprague-Dawley rats, mean weight 150±5 g, fasting since 24 hours, were used.

The salivation was induced by the intraperitoneal administration of 1 mg/kg of carbachole. The products under exam were administered orally one hour before the cholinergic stimulus.

INTERACTION WITH MUSCARINIC RECEPTOR

The activity at the muscarinic receptor level was evaluated by means of displacement, with different concentrations of the compounds under exam, of the $^3H$-QNB bound to the receptors of the rat cerebral cortex according to the method, with minor changes, of H. I. Yamamura and S. H. Snyder—Proc. Nat. Acad. Sci., 71, 1725–1729 (1974).

ACUTE TOXICITY

The acute toxicity was determined by administering by oral route the substances under exam to Swiss mice, average weight 20±2 g. The observation period was 14 days. 10 Animals were used for each assayed dose.

The results are reported in the following Table IV.

TABLE IV

| | PHARMACOLOGICAL ACTIVITY | | | | | | | |
|---|---|---|---|---|---|---|---|---|
| Compound n. | % Antisecretory activity mg/kg p.o. | | | Salivation by carbachol-protection % | Interaction with muscarinic receptor | | | $LD_{50}$ |
| | 6.25 | 12.5 | 25 | 62.5 mg/kg p.o. | $10^{-7}$ | $10^{-6}$ | $10^{-5}$ | mg/kg |
| 2 | 10.3 | 15.1 | 20.4 | 30 | — | 1.0 | 34.0 | >500 |
| 3 | 6.0 | 14.3 | 35.9 | 0 | 3.6 | 14.2 | 58.5 | <500 |
| 4 | 22.7 | 48.1 | 70.3 | 70 | 17.6 | 68.9 | 90.6 | >500 |
| 15 | 9.6 | 27.7 | 41.8 | 10 | 5.7 | 8.9 | 21.0 | >500 |
| 13 | 19.2 | 47.5 | 69.6 | 30 | 2.7 | 22.8 | 80.9 | >500 |
| P | 7.9 | 46.0 | 71.5 | 10 | 12.8 | 57.4 | 90.5 | >2000 |

P = Pirenzepine.

The present invention refers also to all the industrially applicable aspects connected with the use of compounds I in therapy.

An essential aspect of the invention is therefore provided by pharmaceutical compositions, suitable for the oral, parenteral or topical administration, containing as the active principle at least one of the compounds of formula I or one of its pharmaceutically acceptable salts in addition to the carriers usually employed in pharmaceutical technique.

Examples of said compositions are provided by capsules, sugar-coated tablets, tablets, syrups, drops, ointments, sterile vials for injection etc.

We claim:

1. A compound of formula I

[Structure: dibenzo heterocycle with A—B bridge at top, Y at left ring junction, N-R at bottom]   I wherein
Y is N or CH,
A is NH, B is C=O or C=S or vice versa,
R is a group of formula

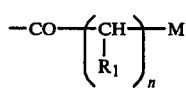

wherein $R_1$ is hydrogen or $C_1$-$C_4$ alkyl and n is 1 or 2, M represents one of the following groups

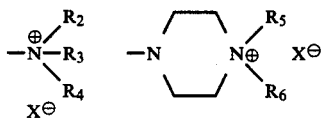

wherein $X^-$ is the anion of an halogenidric acid, $R_2$, $R_3$ and $R_4$, which may be the same or different, represent linear or branched $C_1$-$C_4$ alkyl, $C_3$-$C_7$ cycloalkyl, pivaloyloxymethyl, benzyl or $R_2$ has one of said meanings and $R_3$ and $R_4$ together form one of the following cyclic groups

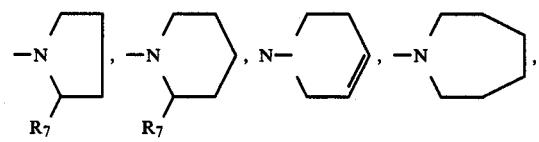

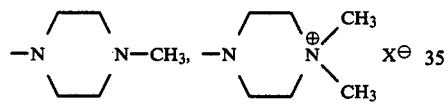

wherein
$R_7$ is hydrogen or methyl and $X^\ominus$ has the above defined meaning, or
$R_2$, $R_3$ and $R_4$, taken together, form one of the following groups:

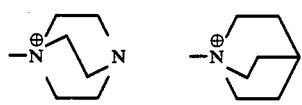

$R_5$ and $R_6$, which can be the same or different, represent methyl, ethyl, benzyl, 3,4-methylenedioxybenzyl or pivaloyloxymethyl.

2. A compound according to claim 1 wherein Y is N, A is NH, B is C=O.

3. A compound according to claim 1 wherein Y is N, A is C=O and B is NH.

4. A compound according to claim 1 wherein Y is CH, A is C=O and B is NH.

5. A compound according to claim 1 wherein n is 1, $R_1$ is hydrogen, M is a group of formula

at least one of the $R_2$, $R_3$ or $R_4$ groups being methyl.

6. A compound according to claim 5 wherein $R_2$ is methyl and $R_3$ and $R_4$ taken together form one of the following cyclic groups

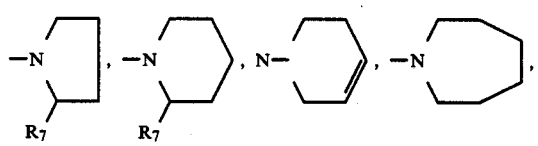

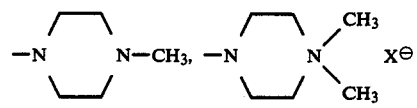

wherein $R_7$ and $X^-$ have the above defined meanings.

7. A compound according to claim 1 wherein $R_2$, $R_3$ and $R_4$ taken together form one of the following groups:

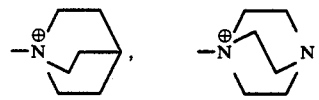

8. A compound according to claim 1 wherein M is a group

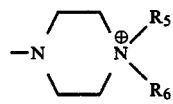

wherein $R_5$ and $R_6$, which may be the same or different, are methyl, ethyl, benzyl, 3,4-methylenedioxybenzyl, pivaloyloxymethyl.

9. A pharmaceutical composition having antiscretoric, antiulcerogenic, spasmolytic and antimuscarinic activities containing as the principal active ingredient an antisecretoric, antiulcerogenic, spasmolytic and antimuscarinic effective amount of a compound according to claim 1 in admixture with a pharmaceutically acceptable carrier.

* * * * *